US009244050B2

(12) United States Patent
Wiacek et al.

(10) Patent No.: US 9,244,050 B2
(45) Date of Patent: Jan. 26, 2016

(54) METHODS AND DEVICES FOR TESTING WATER

(71) Applicant: BAKER HUGHES INCORPORATED, Houston, TX (US)

(72) Inventors: Stephen J. Wiacek, Wallingford, PA (US); Bingbing Guo, Missouri City, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 14/084,035

(22) Filed: Nov. 19, 2013

(65) Prior Publication Data
US 2014/0147923 A1    May 29, 2014

Related U.S. Application Data

(60) Provisional application No. 61/731,184, filed on Nov. 29, 2012.

(51) Int. Cl.
*G01N 33/18* (2006.01)
*G01N 1/28* (2006.01)
*C02F 1/52* (2006.01)

(52) U.S. Cl.
CPC . *G01N 33/18* (2013.01); *C02F 1/52* (2013.01); *C02F 1/5209* (2013.01); *Y10T 436/21* (2015.01); *Y10T 436/25375* (2015.01)

(58) Field of Classification Search
CPC ......... C02F 1/52; C02F 1/5209; G01N 33/18; Y10T 436/21; Y10T 436/25375
USPC ............... 436/39, 40, 60, 163, 164, 167, 168, 436/174, 177, 178, 139; 422/68.1, 73, 422/82.05, 82.09, 88, 527, 547, 556; 73/53.01, 53.05, 53.07, 61.41, 61.71, 73/64.41
See application file for complete search history.

(56) References Cited

U.S. PATENT DOCUMENTS

| | | | |
|---|---|---|---|
| 5,462,669 A * | 10/1995 | Yeh ................................ 210/703 |
| 2004/0217058 A1* | 11/2004 | Cadera et al. ................. 210/649 |
| 2011/0147316 A1* | 6/2011 | Polizzotti et al. ............. 210/705 |
| 2011/0272362 A1* | 11/2011 | Sikes et al. .................... 210/705 |

FOREIGN PATENT DOCUMENTS

WO    2012/065250    *   5/2012

* cited by examiner

*Primary Examiner* — Maureen Wallenhorst
(74) *Attorney, Agent, or Firm* — Mossman, Kumar & Tyler, PC

(57) ABSTRACT

Methods and systems for testing fluid samples include a diffused air flotation (DAF) system and a jar. The jar includes a diffuser for injecting the diffused air into the jar and a tap for drawing a fluid out of the jar.

19 Claims, 2 Drawing Sheets

METHODS AND DEVICES FOR TESTING WATER

CROSS-REFERENCE TO RELATED APPLICATIONS

This application claims priority from U.S. Provisional Application Ser. Application No. 61/731,184 filed Nov. 29, 2012, the disclosure of which is incorporated herein by reference.

BACKGROUND OF THE DISCLOSURE

1. Field of the Disclosure

This disclosure is directed to the methods and devices for testing fluids such as water or waste water.

2. Background of the Art

Water testing may be performed for a variety of reasons such as to evaluate wastewater characteristics before or after treatment, determine whether a water source is suitable for domestic consumption, or suitability of water for industrial uses. One conventional form of testing is jar testing. In typical jar testing, several containers, or jars, are filled with water samples. Each jar may be treated with a different amount of a chemical selected to cause coagulation or flocculation. The samples may be stirred or otherwise agitated and observed for a period of time. The differences in reactions of the several water samples are evaluated during this time. Illustrative effects evaluated may include flocculation, settling, and turbidity. Some tests may also involve dissolved air flotation (DAF). In the DAF process, pressurized water having dissolved air is introduced into a container having a water sample that has chemically treated suspended matter (floc particles or oil and grease). The dissolved air forms tiny bubbles that adhere to the suspended matter, which then floats to the water surface. The floating material and the underlying water may then be tested.

Conventionally, these and other water tests are performed in separate test units, which is cumbersome and may compromise the quality of the tests as water samples are moved between test units. The present disclosure addresses the need to have a more efficient method and device for testing fluids such as water or waste water.

SUMMARY OF THE DISCLOSURE

In aspects, the present disclosure provides a method of testing a liquid sample. The method may include treating a liquid sample in a jar with at least one chemical agent to induce flocculation in the liquid sample, introducing dissolved air and carrier water into the liquid sample in the jar to float floc to a liquid surface in the jar, and drawing a supernate sample from the jar.

In aspects, the present disclosure may include a system for testing a liquid sample. The system may include a diffused air flotation (DAF) system configured to supply diffused air and a jar having an interior volume defined by a vertical wall and base. The jar may include a diffuser disposed on the wall that receives the diffused air and carrier water from the DAF system via a fluid line. The diffuser may include a flow bore for injecting the diffused air into the interior volume. The jar also may include a tap disposed on the wall that draws a fluid out of the interior volume.

Examples of certain features of the disclosure have been summarized (albeit rather broadly) in order that the detailed description thereof that follows may be better understood and in order that the contributions they represent to the art may be appreciated. There are, of course, additional features of the disclosure that will be described hereinafter and which will form the subject of the claims appended hereto.

BRIEF DESCRIPTION OF THE FIGURES

For detailed understanding of the present disclosure, reference should be made to the following detailed description, taken in conjunction with the accompanying drawing.

DETAILED DESCRIPTION OF THE DISCLOSURE

The present disclosure relates to methods and devices for testing water. While the present disclosure may be applied to a variety of applications, for brevity, the present disclosure will be discussed in the context of performing one or more tests on wastewater.

Figure 1:
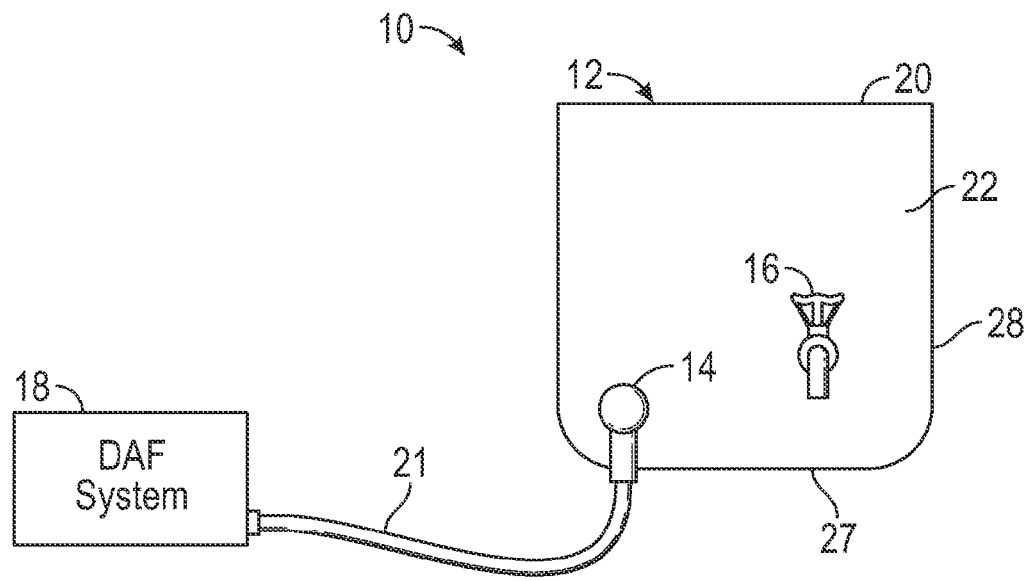
FIG. 1 illustrates a water testing system according to one embodiment of the present disclosure.

Referring now to FIG. 1, there is shown one embodiment of a test system 10 for performing multiple tests on a fluid sample. For convenience, water will be used as an illustrative liquid. The system 10 may include a jar 12, a feed inlet 14, a tap 16, and a dissolved air flotation (DAF) system 18. The feed inlet 14 and the tap 16 are positioned on the vertical wall of the jar 12 to provide controlled fluid communication with the water in the jar 12. The feed inlet 14 and the tap 16 may be permanently or removable disposed on the wall of the jar 12. As will be described in greater detail below, this arrangement enables a variety of treatments and tests to be performed on a water sample in an efficient sequential fashion. This arrangement also allows these tests and treatments to be performed without transferring the water sample between two or more different test devices.

The jar 12 may be a container suitable to receive and hold liquids such as water. For lab environments, the jar 12 may be sized to receive about two liters of liquids. However, the jar 12 is not limited to any particular volume. The jar 12 may include an open top 20 through which a water sample may be poured into an interior 22 of the jar 12. The jar 12 may be formed of any material (e.g., plastic, fiberglass, composites, metal, etc.). In some embodiments, the jar 12 has some portions that are sufficiently transparent in order to observe the condition of the water sample. In some embodiments, the open top 20 may be configured to allow a suitable mixer or agitator 44 (FIG. 2) to be positioned in the interior 22. The agitator 44 (FIG. 2) may include an electric motor that moves (e.g., rotates or translates) one or more paddle member 45. The paddle member 45, may be a plate, blade, rod, disk, or other suitable member that can cause fluid movement. Also, the open top 20 may be configured to receive a sealing lid (not shown). An advantage of an open top 20 is for ease of cleaning, which can be made more difficult by the stickiness of some flocculent layers 40. Another benefit of having an open top jar is for the convenience of addition additional coagulants or flocculants as necessary. While the jar 12 is shown as being generally rectangular and defined by a bottom 27 and a vertical wall 28 having four sides, the jar 12 may have any shape (e.g., rectangular, cylindrical, etc.).

The DAF system 18 may be configured to supply a controlled quantity of a carrier fluid (e.g., water) having dissolved air. The DAF system 18 may be a conventional system that includes an air compressor and water effluent source. The DAF system 18 may be connected to the feed inlet 14 by a fluid 21, which may be a hose or tube. It should be understood that the teachings of the present disclosure is not limited to any particular DAF system 18. That is, any system capable of delivering air that can be released into the jar interior 22 for flotation of solids may be used.

Figure 2:
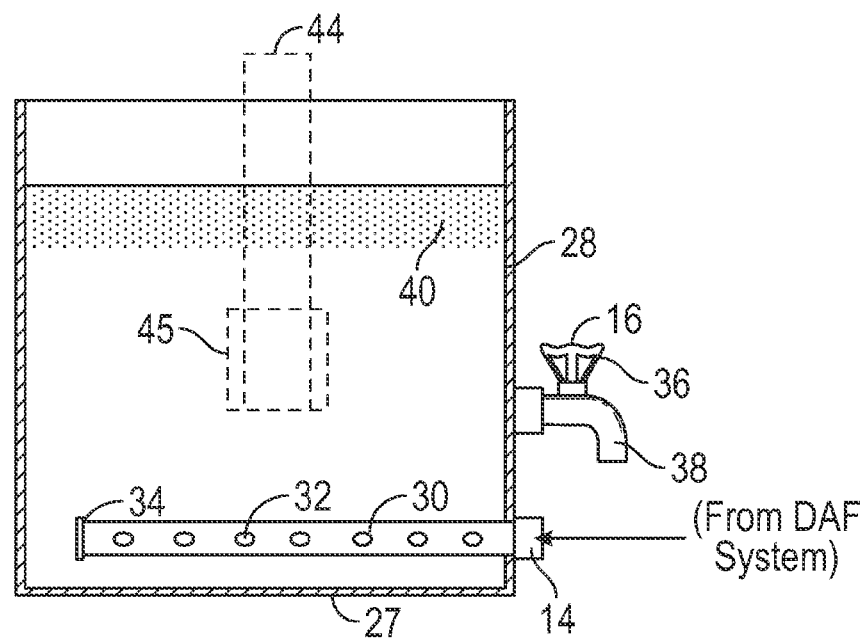
FIG. 2 illustrates one example of a jar for use with the water testing device according to one embodiment of the present disclosure.

Referring now to FIG. 2, there are shown further features of the jar 12. In some embodiments, the feed inlet 14 is fixed on the vertical wall 28 of the jar 12 and may be connected to a diffuser 30 that is positioned inside the jar 12. The diffuser 30 distributes the pressurized water over a relatively large area using multiple distributed points near the bottom wall 27. In some embodiments, the diffuser 30 may be a tubular member that has a series of axially spaced-apart openings 32. Also, an end 34 of the diffuser 30 may be closed or capped to force all the pressurized water out of the openings 32. While the diffuser 30 is shown as one straight tube, it should be appreciated that any shape (e.g., curved or circular) and any number of diffusers 30 may be used to distribute dissolved air in the interior 22 of the jar 12.

The tap 16 is fixed to the vertical side wall 28 of the jar 12 and may be used to retrieve supernate samples. The tap 16 may include a knob 36 that actuates a valve (not shown) that selectively blocks flow along a spout 38 of the tap 16. In some embodiments, the tap 16 is positioned at a height that is well below the expected height of the flocculent layer 40 that floats on the surface of the water sample. In some embodiments, the height may be below the midway height of the jar 12.

Figure 3:
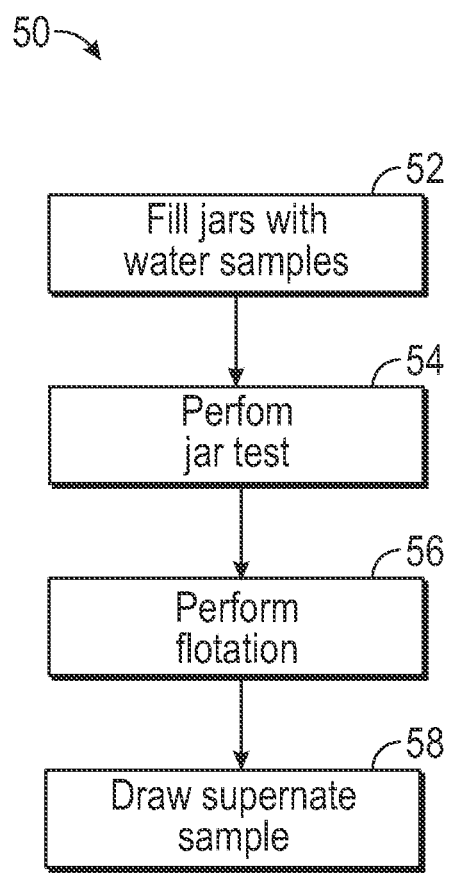
FIG. 3 illustrates a method for testing water according to one embodiment of the present disclosure.

Referring now to FIG. 3, there is shown one method 50 for testing water according to the present disclosure. The method 50 will be discussed with reference to embodiments shown FIGS. 1 and 2. The method 50 may be used in a laboratory or in the field, such as at a drilling rig or any facility where water testing may need to be performed.

Some conventional water tests are comparative tests wherein water samples are treated with different amounts of one or more agents. Therefore, at step 52, a known amount of water samples is poured into a plurality of jars 12. Of course, the method 50 may be performed using a single jar 12 in other test regimes. For the jars 12 of FIGS. 1 and 2, the water samples may be poured through the open top 22.

At step 54, a jar test may be initiated. In one non-limiting example of a jar test, a specified amount of one or more agents is added to each of the jars 12. The agent(s) may be added through the top of the jar 12. The agents may be selected to react in a specified manner with the water sample. For example, the agents may be selected to cause coagulation or flocculation of solids in the water sample. That is, relatively small solid particles may be caused to interact and form larger clumps of solids or form floc. Illustrative agents include, but are not limited to, emulsion polymers, solution polymers, inorganics, liquid coagulants, alum, etc. A different amount or dosage of agent(s) may be introduced into each of the jars. During this step, the water samples may be agitated using a mechanical mixer 44 positioned in the jar interior 22 to disperse the agent(s) homogenously into the water samples.

The reactions of the water samples in the jar 12 are compared to one another to determine the most appropriate dosage of a particular agent or agents. Other test parameters, such as mixing rate or temperature may also be varied for the several test samples. The reaction of the water samples may be observed over a desired period of time. Illustrative, but not exclusive criteria, that may be evaluated include: flotation rate, floc separation, supernate clarity or turbidity.

After jar testing is complete, the flotation of the solids in the water sample is initiated at step 56. Because the jar 12 already has an inlet 14 for introducing dissolved air and carrier water into the jar 12, the flotation step may be performed without transferring the water sample(s) to a different container or device. When the DAF system 18 is started, pressurized water exits the diffuser 30. The dissolved air in the pressurized carrier water escapes as tiny air bubbles that attach to the floc or other solids suspended in the water sample. It should be appreciated that the diffuser 30 distributes the dissolved air throughout a relatively large lower area of the jar 12, which enables a larger volume of the water sample to be exposed to the dissolved air than a single injection point. Eventually, the solids and attached air bubbles float to the surface of the water sample. An illustrative layer of flocculent is labeled with numeral 40. While the methodology may vary depending on the nature of the sample being tested, in some embodiments, the dissolved air may be introduced into the liquid sample at a rate between about 100-250 mls to each jar over a period of 5 to 10 seconds and about 20 to 25 mL/second 20 to 25 mL/second.

At step 58, the tap 16 may be opened to draw off a supernate sample from the jar 12. The tap 16 is at a height lower than the floating solids 40. Therefore, the supernate sample may be taken without disturbing the solids floating at the water surface. As with step 56, this step may also be performed without transferring the water sample(s) to a different container or device. The supernate sample may then be evaluated for turbidity and/or other water characteristics.

It should be understood that the method 50 is merely illustrative of the type of tests that may be sequentially performed on a water sample without transferring the water sample between two or more test devices. Thus, methods according to the present disclosure may include tests and treatments that are the same as, similar to, or different from the method 50. A common feature of such methods is that a plurality of tests and/or treatments may be performed before removing the water sample from the jar 12.

In one non-limiting example, the liquid sample is water, and in a different non-restrictive embodiment the liquid sample is a mixture of a hydrocarbon and water. A typical mixture of a hydrocarbon and water would be an emulsion, such as an oil-in-water emulsion or a water-in-oil emulsion or a bi-continuous emulsion. The testing conducted in the jar 12 may be to determine the rapidity or completeness of separation of the oil from the water using one or more chemical agents. A measure of the effectiveness of separation of oil from water is the thickness and/or appearance of flocculent layer 40. In another non-limiting embodiment, the oil is crude oil. As used above, the term "water" refers generally any liquid that in which water is a significant component (e.g., brine, seawater, etc.).

While the foregoing disclosure is directed to the preferred embodiments of the disclosure, various modifications will be apparent to those skilled in the art. It is intended that all variations within the scope of the appended claims be embraced by the foregoing disclosure.

We claim:

1. A method of testing a liquid sample, comprising:
introducing the liquid sample into multiple jars;
treating the liquid sample in the jars with at least one chemical agent to induce flocculation in the liquid sample, wherein the liquid sample in each jar is treated with a different dosage of at least one chemical agent;
comparing the liquid samples in each jar to determine a dosage of the at least one chemical agent that results in a predetermined level of at least one of: (i) flotation rate, (ii) floc separation, (iii) clarity, and (iv) turbidity;
agitating the liquid sample in each jar after treating the liquid sample with at least one chemical agent selected to cause flocculation of solids in the liquid sample;
introducing dissolved air and carrier water into the liquid sample in each jar to float floc to a liquid surface in the jars;
drawing a supernate sample at a height lower than the floating floc from each jar after introducing dissolved air and carrier water into the liquid sample; and
evaluating each supernate sample for at least turbidity.

2. The method of claim 1, wherein the dissolved air is supplied through an inlet disposed on a wall of the jars.

3. The method of claim 1, wherein the dissolved air is introduced into the liquid sample at multiple locations inside the jars.

4. The method of claim 1, wherein the dissolved air is introduced into the liquid sample at a rate between about 100-250 milliliters over a period of 5 to 10 seconds and about 20 to 25 milliliters per second.

5. The method of claim 1, wherein the supernate sample is drawn through a tap disposed on a wall of the jars.

6. The method of claim 1, wherein the supernate sample is drawn without penetrating a flocculent layer floating at a surface of the liquid sample.

7. The method of claim 1, further comprising evaluating the treated supernate sample for at least one of: (i) pH, (ii) alkalinity, (iii) particle count, (iv) oil, and (v) grease.

8. The method of claim 1, wherein the liquid sample is one of (i) a water sample, and (ii) a waste water sample.

9. The method of claim 1, wherein the liquid sample is a mixture of a hydrocarbon and water.

10. The method of claim 1, wherein the jars have an open top.

11. The method of claim 1, wherein the jars are rectangular.

12. The method of claim 1, wherein the dissolved air and carrier water are introduced using a diffuser that distributes pressurized water using multiple distributed points at a bottom of the jars.

13. The method of claim 1, further comprising varying a mixture rate of the liquid samples during agitation.

14. A system for testing a liquid sample, comprising:
a diffuse air flotation (DAF) system configured to supply diffused air and carrier water via a fluid line;
a transparent jar having an interior volume defined by a vertical wall and base, the jar including:
a diffuser disposed on the wall and receiving the diffused air and carrier water received from the DAF system via the fluid line, the diffuser including a flow bore for injecting the diffused air and carrier water into the interior volume;
a tap disposed on the wall, the tap being configured to selectively draw a fluid out of the interior volume; and
an agitator positioned in the interior volume, the agitator having at least one moving paddle member.

15. The system of claim 14, wherein the diffuser includes an elongate body disposed in the interior volume and a plurality of openings that inject the diffused air into multiple locations in the interior volume, wherein the DAF system includes an air compressor and a water effluent source, wherein the vertical wall is at least partially transparent, and wherein the jar has an open top.

16. The system of claim 14, further comprising multiple transparent jars.

17. A method of testing a liquid sample, comprising:
introducing the liquid sample into a transparent jar;
treating the liquid sample in the jar with at least one chemical agent to induce flocculation in the liquid sample;
agitating the liquid sample using a paddle member disposed in the jar and after treating the liquid sample with at least one chemical agent.
introducing dissolved air and carrier water into the liquid sample in the jar to float floc to a liquid surface in the jar, the dissolved air being supplied through an inlet disposed on a wall of the jar and being introduced at multiple locations insider the jar;
drawing a supernate sample from a tap disposed on a wall of the jar after the introducing the dissolved air and carrier water into the liquid sample, wherein the supernate sample is drawn without penetrating a flocculent layer floating at a surface of the liquid sample from the jar; and
evaluating the drawn supernate sample after the agitation for at least one of: (i) turbidity, (ii) pH, (iii) alkalinity, (iv) particle count, (v) oil, and (vi) grease.

18. The method of claim 17, further comprising:
introducing the liquid sample into multiple jars;
treating the liquid sample with a different dosage of at least one chemical agent in each jar;
agitating the liquid sample in each jar;
introducing dissolved air and carrier water into each jar; and drawing the supernate sample after the agitation from each jar.

19. The method of claim 17, further comprising determining a dosage of at least one chemical agent based at least on the evaluated supernate sample.

* * * * *